United States Patent [19]
Hausler

[11] 4,349,536
[45] Sep. 14, 1982

[54] METHOD OF PROMOTING SUNTAN USING A CREAM CONTAINING ZINC AND COPPER SALTS

[76] Inventor: Kenneth J. Hausler, 401 Alderley St., Toowoomba, Queensland 4350, Australia

[21] Appl. No.: 255,940

[22] Filed: Apr. 20, 1981

Related U.S. Application Data

[63] Continuation of Ser. No. 129,290, Mar. 11, 1980, abandoned, which is a continuation of Ser. No. 16,574, Mar. 1, 1979, abandoned, which is a continuation-in-part of Ser. No. 886,194, Apr. 18, 1978, abandoned.

[51] Int. Cl.³ .................. A61K 7/42; A61K 33/30; A61K 33/34
[52] U.S. Cl. .................. 424/59; 424/141; 424/143; 424/145
[58] Field of Search .................. 424/59, 143, 145, 141

[56] References Cited

U.S. PATENT DOCUMENTS 3,551,554 12/1970 Herschler .................. 424/7
3,896,238 7/1975 Smith .................. 424/358
3,923,982 12/1975 Lamand et al. .................. 424/140

FOREIGN PATENT DOCUMENTS 964,444 7/1964 United Kingdom .

OTHER PUBLICATIONS

Handbook of Nonprescription Drugs, 5th ed., pp. 317-323 (1977).
Chemical Abstracts 79:132953d (1973), 77:110219a (1972), 79:1223081 (1973), 77:109,236x (1972).
McCutcheon's Detergents & Emulsifiers, 1973, p. 150.

Primary Examiner—Leonard Schenkman
Attorney, Agent, or Firm—Mark Dryer

[57] ABSTRACT

A method of selectively absorbing through the membranes of the cells of the human skin the trace mineral cations, zinc (II) and copper (II), in a non-irritating body; by incorporating the salts of such trace minerals into an oil-in-water cream base, emulsified with the alkali metal or alkaline-earth metal salts of anionic surfactants. The cream is applied to the human skin and has a beneficial effect which cannot be obtained by the oral administration of such trace minerals in oral dosage form and usual dosage range.

4 Claims, 3 Drawing Figures

METHOD OF PROMOTING SUNTAN USING A CREAM CONTAINING ZINC AND COPPER SALTS

CROSS REFERENCE TO RELATED APPLICATIONS

This application is a continuation of U.S. Patent Application Ser. No. 129,290 filed on Mar. 11, 1980 (now abandoned) which is a continuation of Patent Application Ser. No. 016,574 filed Mar. 1, 1979 (now abandoned). Application Ser. No. 016,574 is a continuation-in-part of U.S. Patent Application Ser. No. 886,194 filed Apr. 18, 1978, now abandoned.

BACKGROUND OF THE INVENTION

The present invention relates to a method for selectively absorbing through the human skin the trace mineral cations, zinc(II), and copper (II), in a manner which does not alter the permeability of the human skin to ions in general, thus avoiding any resulting inflammatory reaction which occurs when the permeability of the human skin to ions in general is altered; and also in a manner which will leave the ions free inside the cells to act as enzyme activators, or function as electrophilic agents, for beneficial therapeutic use not being obtained by the administration of the corresponding trace minerals in oral or parenteral dosage form, and usual dosage range.

U.S. Pat. No. 3,923,982 teaches intramuscular and subcutanaceous injection of oil suspensions of copper, zinc and manganese compounds in herd animals to overcome trace element deficiency. The present invention on the other hand does not treat or prevent trace mineral deficiencies in humans but enables cations of zinc(II), and copper(II) to be transported across the membranes of the epidermis and dermis for a beneficial therapeutic use which is not obtained by administration of zinc, and copper compounds orally or parenterally in the usual dosage ranges.

Vashilinko et al., Farmatsiya, (Moscow), (1973), 22 (4), 26-30 teach that the drugs, sodium sulfacyl and potassium iodide, are released into the skin and blood more rapidly when prepared in an emulsion base containing sodium lauryl sulfate than when prepared in an emulsion base stabilized with lanolin. This refers to the complex action of surfactants in general on drug absorption and show how the absorption of drugs can be altered by the use of surfactants. But this only refers to drugs that are absorbed through the skin to a certain extent normally, and shows that this absorption can be increased by the use of surfactants. It does not show that the divalent cations zinc(II), and cooper(II), can be selectively absorbed through the skin without altering the permeability of the skin to ions in general, whereas this invention shows how this can be achieved, and it shows the exact mode of action of such a trace mineral cream.

Dugard et al., J Invest.Dermatol. (1973), 60 (5) 263-9, and Riker et al., Acta Fac. Med. Univ. Burn. (1972) 40 (Pt. 1) 177-80 both teach the skin permeability of ionic surfactants and their effects on the permeability of the human epidermis, and their significance for the absorption of certain ions. But both of these investigations were carried out, in vitro, to demonstrate the possible toxicological effects of surfactants. Dugard et al show that solutions of ionic surfactants (both anionic and cationic) increased the permeability of isolated epidermal membranes. But it is a well known fact that substances that increase the permeability of human skin to ions in general also cause skin damage and there is a distinct relationship between the damage caused to the skin and the increased permeability of human skin, as shown by increases in a.c. conductance across isolated epidermal membranes.

SUMMARY OF THE INVENTION

The present invention provides a method for promoting suntan comprising topical administration to areas of skin exposed to ultra-violet radiation of an effective amount of a composition for selectively transporting zinc (II) and copper (II) cations across the membranes of human epidermis and dermis, said composotion consisting essentially of 0.1 to 1.0% by weight of each of zine (II) sulfate and copper (II) sulfate in an oil-in-water cream base containing between about 0.5% and 2% by weight, based upon the total weight of said composition of at least one topically acceptable anionic surfactant selected from the group consisting of alkali metal and magnesium salts of sulfuric acid esters of $C_{10}$ to $C_{14}$ fatty acid alcohols.

Preferred are compositions containing 0.2% zine (II) and 0.2% copper (II) sulfate. These compositions are especially useful in promoting suntan.

The preferred anionic surfactants used in the present invention are derived from the sulfuric acid esters of $C_{10}$ to $C_{14}$ fatty acid alcohols. Especially preferred are sodium or magnesium salts, such as, for example, the sodium or magnesium lauryl sulfates.

BRIEF DESCRIPTION OF THE DRAWINGS

The above and other features and advantages of the present invention will become further apparent from the following description, reference being made to the accompanying drawings in which.

DETAILED DESCRIPTION OF THE INVENTION

Figure 1:
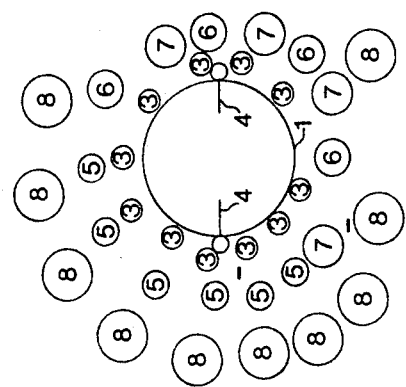
FIG. 1 illustrates an oil droplet in an aqueous environment approaching a cell wall.
Figure 1:
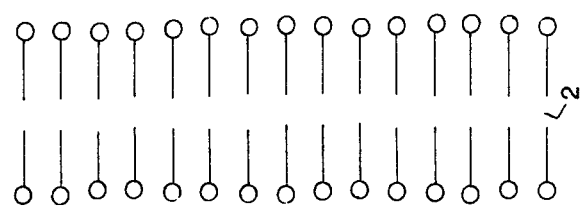

It is believed that the different reaction to solar ultraviolet radiation that occurs in the fair-skinned individual as compared to the darker-skinned individual is due to a "slower" rate of transfer of the trace mineral cations zinc(II), copper(II), from storage sites in the body to the cells of the epidermis and dermis, in a fair-skinned individual as compared to such rate of transfer in the darker-skinned individuals. These two trace mineral cations were chosen on the basis that (1) tyrosinase, the enzyme that initiates the production of melanin from tyrosine in the melanocytes, is a copper-containing enzyme and requires the copper ion for activation; and (2) that zinc ions may inhibit inflammatory reactions through various mechanisms, including the stabilisation of lysosomal membranes, and inhibition of prostaglandin synthesis.

The present invention resides in the discovery that the reaction of fair-skinned individuals to solar ultraviolet radiation may be altered by devising a trace mineral cream, so that, when applied to the skin, would achieve the transport of these mineral cations, zinc(II) and copper(II), across the membranes of the cells of the epidermis and dermis, so that they can act as enzyme activators, or function as electrophilic agents.

To test these hypotheses a trace mineral cream was devised to conform to the following principles:

(A) That a method be devised to set a limit to the maximum amount of the trace mineral cations that would be absorbed across the cell membranes of the cells of the epidermis and dermis. The reasons for setting a limit to the maximum amount that would be absorbed are:

(a) To reduce the possibility of any adverse reaction to such a formulation.

(b) On theoretical grounds that, by using a method that sets a limit to the maximum absorbed, it would be more likely that a successful method could be devised for transporting the trace mineral cations, zinc(II) and copper(II) across the membranes of the cells of the epidermis and dermis. (B) That the method used would not depend on increasing the permeability of human skin by the use of either cationic or anionic surfactants, in sufficient strengths, as this would cause a considerable inflammatory response.

In formulating this trace mineral cream, it was decided to use, as a method of limiting the maximum amount that would be absorbed, a process of absorbing these trace mineral cations by the method of transporting them across the cell membranes, attached to the surface of oil-droplets, in an oil-in-water cream. This method of attachment would have to be one that existed only during the period of time required for the oil-droplets to diffuse across the lipid portions of the cell membranes, so that once across the cell membranes, the trace mineral cations would be free to act as ions in the aqueous environment of the cell's interior, and thus act as enzyme activators, or function as electrophilic agents.

Because of the fact that an ionic bond in an aqueous environment is different from the ionic bond in a lipid environment, it was decided that it should be possible to transport the cations, zinc(II), and copper(II) across the cell membranes, by using an oil-in-water cream base, using as an emulsifying agent sodium or magnesium salt of an anionic surfactant e.g. sodium or magnesium lauryl sulfate.

The following formulation listed in Table I can be prepared in the usual manner, known to any person skilled in the art of pharmaceutical formulation.

TABLE I

| Component | Formulation 1 | Formulation 2 |
| --- | --- | --- |
| Zinc(II) sulfate | 0.2% | 0.6% |
| Copper(II) sulfate | 0.2% | — |
| Sodium lauryl sulfate | 1.0% | 1.0% |
| Cetostearyl alcohol | 9.0% | 9.0% |
| White Soft Paraffin | 15.0% | 15.0% |
| Liquid Paraffin | 5.0% | 5.0% |
| Chlorocresol | 0.03% | 0.03% |
| Water to | 100.0% | 100.0% |

Figure 2:
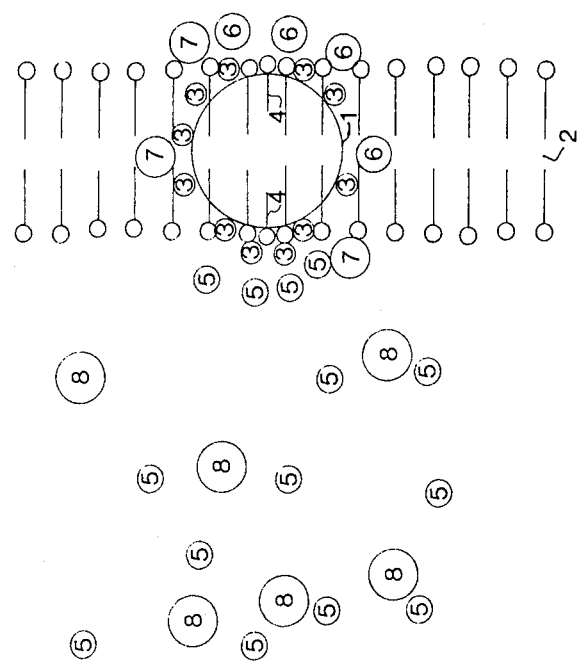
FIG. 2 illustrates the oil droplet being transported across the cell wall.
Figure 3:
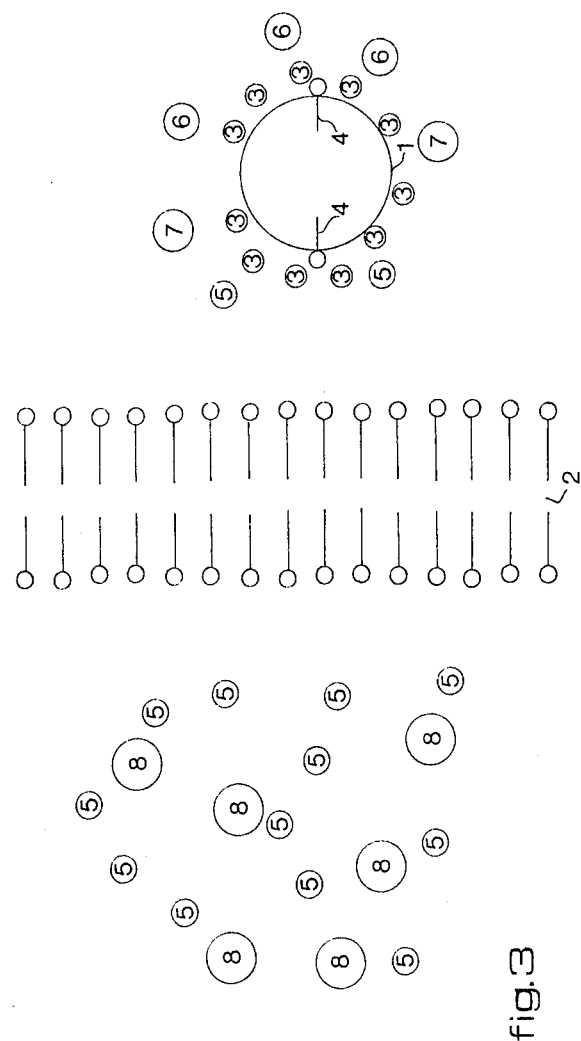
FIG. 3 illustrates the oil droplet within the cell.

The theoretical basis for the mode of action of this formulation is as follows:

As shown in FIG. 1, an oil-droplet 1 is approaching the cell membrane (membrane lipid bilayer) 2 with velocity (v), and has a number of negative charges 3 on its surface due to the polar part of sodium lauryl sulfate 4. Surrounding the oil-droplet 1 there are a number of sodium 5, copper 6, zinc 7 and sulfate 8 ions in the aqueous phase. As the oil-droplet 1 moves across the lipid membrane 2 it loses its water structure surrounding it, and this is reformed on the other side of the membrane (i.e. the cell's interior). As the oil-droplet 1 cannot diffuse across the membrane 2 with the negative charges 3 on its surface unneutralised, it will pull across the membrane with it a sufficient number of cations 5, 6, 7 to neutralise the negative charges on its surface. Because of the relative standard electrode potentials, and ionic radii (see Table II below) of the cations present, the copper 6 and zinc 7 ions present and sufficient number of sodium 5 ions to balance the remaining number of negative charges 3 on its surface, will be pulled across the membrane 4, by the oil-droplet 1. (FIG. 2). Once across the membrane 2 (FIG. 3) the oil-droplet 1 will regain its water structure about it and the cations 5, 6, 7 on its surface will be free to diffuse into the surrounding water, and the zinc 6 and copper 7 cations present will be free to act as enzyme activators, or function as electrophilic agents.

TABLE II

| Ion | Standard Electrode Potential (V) | Ionic Radius (nm) |
| --- | --- | --- |
| Cu(II) | +0.34 | 0.072 |
| Zn(II) | −0.76 | 0.074 |
| Na(I) | −2.71 | 0.097 |

Another method of showing the selective mode of action of the invention is to consider entropy changes. The entropy of hydration of ions is a large negative number, and it gets more negative the more highly charged an ion is and the smaller its radius e.g. sodium is $-87.4$ J deg$^{-1}$, mol$^{-1}$, and zinc is $-267.8$ J deg$^{-1}$, mol$^{-1}$. According to the second law of thermodynamics, for spontaneous change to occur in an isolated system, the entropy must increase, therefore, as the oil-droplet moves across the lipid membrane the ion that it will pull across first will be the one that gives the greatest increase in entropy by the loss of its water of hydration. Therefore, zinc ions ($-267.8$) will be selectively absorbed across the membrane before the sodium ions ($-87.4$).

The following tests were carried out on fair-skinned human volunteers to demonstrate the effectiveness of compositions according to the invention for the prevention and treatment of sunburn. Comparison tests were carried out between fair-skinned and darker-skinned individuals, exposed to identical conditions of exposure to solar ultraviolet radiation, by using a trace mineral cream containing 0.2% w/w of both zinc sulfate and copper sulfate in an oil-in-water cream base using sodium lauryl sulfate as an emulsifying agent. This cream was applied and rubbed in both before and after exposure, each day for a number of days, by the fair-skinned subjects.

It was found that in all cases the reaction to solar ultraviolet radiation in the fair-skinned individuals was altered, compared to their reaction when the cream was not used. Their reaction was similar to that of the darker-skinned subjects and they were able to promote a good tan after a similar exposure, as compared to the moderate erythema, peeling and absence of a good tan that occurred when the cream was not used.

To demonstrate that the action of the trace mineral cream was as described in its mode of action, a trace mineral cream was prepared containing 0.2% w/w of both zinc sulfate and copper sulfate in an oil-in-water cream base, using in place of sodium lauryl sulfate, the cationic surfactant, cetyltrimethylammonium bromide. This cream was used by the fair-skinned subjects under the same conditions under which a trace mineral cream emulsified with sodium lauryl sulfate was used, and it was found to be completely ineffective in altering the reaction to solar ultraviolet radiation of the fair-skinned subjects.

The previous description refers to only one possible use of a trace mineral cream, but one that can be most easily substantiated. In general the proposed use of this invention is for any condition in which it can be shown to have a beneficial effect on the metabolism of the cells of the epidermis, and dermis. As applies to the actual use described, any further proposed uses would be based on the assumption that it is possible to produce a beneficial effect on the metabolism of the cells of the epidermis and dermis by external application of a trace mineral cream that could not also be produced by oral use of such trace minerals in their usual dosage range.

In the present invention if any attempt is made to absorb ions across the human skin by the use of surfactants in sufficient strengths to alter the permeability of human skin, a considerable inflammatory response occurs, and one of the objects of this invention was to specifically devise a method of selectively absorbing the trace mineral cations zinc(II), and copper(II), across the membranes of the cells of the human skin, that would not depend on increasing the permeability of the human skin to ions in general, by the use of either anionic or cationic surfactants in sufficient strengths. In the present invention it has been shown how it is possible to selectively absorb the said trace mineral cations across the membranes of the cells of the human skin, without altering the permeability of the skin to ions in general; thus avoiding any resulting inflammatory response.

The claimed compositions and methods are capable of wide variation and modification and any minor departure or extension is considered as being within the skill of the artisan and as falling within the spirit and scope of this invention.

What I claim is:

1. A method for promoting sun tan comprising topical administration to areas of skin exposed to ultraviolet radiation of an effective amount of a composition for selectivity transporting zinc (II) and copper (II) cations across the membranes of human epidermis and dermis, said composition consisting essentially of 0.1 to 1.0% by weight of each of zinc (II) sulfate and copper (II) sulfate in an oil-in-water cream base containing between about 0.5% and 2% by weight, based upon the total weight of said composition, of at least one topically acceptable anionic surfactant selected from the group consisting of alkali metal and magnesium salts of sulfuric acid esters of $C_{10}$ to $C_{14}$ fatty acid alcohols.

2. The method of claim 1 wherein said anionic surfactant is sodium lauryl sulfate or magnesium lauryl sulfate.

3. The method of claim 1, wherein each of the zinc (II) sulfate and copper (II) sulfate is present in said composition in a concentration of 0.2% by weight.

4. The method of claim 1, wherein the composition administered consists of 0.2% by weight of zinc (II) sulfate, 0.2% by weight of copper (II) sulfate, 1.0% by weight of sodium lauryl sulfate, 9.0% by weight of cetostearyl alcohol, 15.0% by weight of white soft paraffin, 5.0% by weight of liquid paraffin, 0.03% by weight of chlorocresol and water to 100% by weight.

* * * * *